United States Patent
Satou et al.

(10) Patent No.: US 11,491,996 B2
(45) Date of Patent: Nov. 8, 2022

(54) MOVABLE OBJECT CONTROL SYSTEM

(71) Applicant: DAIKIN INDUSTRIES, LTD., Osaka (JP)

(72) Inventors: Naoyuki Satou, Osaka (JP); Masanori Ohsawa, Osaka (JP); Yu Ota, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 420 days.

(21) Appl. No.: 16/615,285

(22) PCT Filed: Feb. 13, 2018

(86) PCT No.: PCT/JP2018/004791
§ 371 (c)(1),
(2) Date: Nov. 20, 2019

(87) PCT Pub. No.: WO2018/220903
PCT Pub. Date: Dec. 6, 2018

(65) Prior Publication Data
US 2020/0122739 A1    Apr. 23, 2020

(30) Foreign Application Priority Data

May 31, 2017  (JP) ................ JP2017-107298

(51) Int. Cl.
| | |
|---|---|
| *B60W 50/00* | (2006.01) |
| *F24F 11/62* | (2018.01) |
| *A61B 5/021* | (2006.01) |
| *A61B 5/08* | (2006.01) |
| *A61G 5/04* | (2013.01) |

(Continued)

(52) U.S. Cl.
CPC ......... *B60W 50/0098* (2013.01); *A61B 5/021* (2013.01); *A61B 5/0816* (2013.01); *A61G 5/04* (2013.01); *F24F 11/62* (2018.01); *G05D 1/0212* (2013.01); *B60W 2540/22* (2013.01); *B60W 2555/20* (2020.02); *F24F 2120/12* (2018.01)

(58) Field of Classification Search
None
See application file for complete search history.

(56) References Cited

U.S. PATENT DOCUMENTS

| | | | |
|---|---|---|---|
| 5,555,512 A | 9/1996 | Imai et al. | |
| 10,126,747 B1 * | 11/2018 | Svec | ............ G16Z 99/00 |

(Continued)

FOREIGN PATENT DOCUMENTS

| | | |
|---|---|---|
| JP | 2513005 B2 | 7/1996 |
| JP | 2978374 B2 | 11/1999 |

OTHER PUBLICATIONS

Extended European Search Report, dated Aug. 31, 2020, for European Application No. 18808721.7.

(Continued)

*Primary Examiner* — Adam D Tissot
*Assistant Examiner* — Garrett F Evans
(74) *Attorney, Agent, or Firm* — Birch, Stewart, Kolasch & Birch, LLP

(57) ABSTRACT

A plurality of thermal areas (11a, 11b, 11c, and 11d) of different thermal environments are formed in a room (11). When it is determined that a person (13) riding on a movable object (20) is feeling uncomfortable in the thermal area (11d), the movable object (20) is remotely operated to move toward the thermal area (11a) where the person (13) feels comfortable.

6 Claims, 3 Drawing Sheets

(51) Int. Cl.
*G05D 1/02* (2020.01)
*F24F 120/12* (2018.01)

(56) References Cited

U.S. PATENT DOCUMENTS

2014/0138043 A1* 5/2014 Matsumoto ........... F24F 1/0057
  165/11.1
2017/0266069 A1* 9/2017 Lozano ................. A61G 5/045

OTHER PUBLICATIONS

International Search Report, issued in PCT/JP2018/004791, PCT/ISA/210, dated May 15, 2018.

* cited by examiner

MOVABLE OBJECT CONTROL SYSTEM

TECHNICAL FIELD

The present invention relates to a movable object control system.

BACKGROUND ART

There are conventionally known air conditioners that control the operation to make an air conditioning state comfortable in an area where a person is located in a room (see, for example, PTL 1 and PTL 2).

PTL 1 discloses a configuration for performing an air conditioning operation with improved quick warming performance by controlling a blow-out direction of conditioned air on the basis of a position where a person is detected and by causing, for example, during heating, heated air to flow along a floor surface in the area where the person is detected to increase a temperature at this floor surface.

In addition, PTL 2 discloses a configuration for performing set-temperature-based control in accordance with a relationship among a position where a person is detected, a temperature at a floor surface around the person, and a room temperature so that the room temperature reaches a set temperature under normal conditions and for changing a direction of air on the basis of the detection result of the position of the person.

CITATION LIST

Patent Literature

PTL 1: Japanese Patent No. 2513005
PTL 2: Japanese Patent No. 2978374

SUMMARY OF INVENTION

Technical Problem

However, the configurations in which air conditioning performed by an air conditioner is controlled in accordance with a position of a person who is present in a room as in the related art have problems that it takes time for the room temperature to reach a temperature at which the person feels comfortable and if the person moves from the position while the temperature is being adjusted, the air conditioning control ends up useless.

In addition, there is a problem that in an environment, for example, an office, where many persons are present in the same area, it is difficult to create an optimum temperature environment for each of the persons who are at neighboring positions.

The present invention is made in view of such problems and an object thereof is to enable thermal environments in which persons in a room feel comfortable to be provided individually.

Solution to Problem

Aspects of the present disclosure are intended for a movable object control system including a movable object (20) movable in a room (11) with a person (13) riding thereon, and a movable object control unit (33) that controls an operation of the movable object (20), and provide the following solutions.

Specifically, according to a first aspect, the movable object control system includes a comfort determination unit (32) that determines comfort of the person (13) riding on the movable object (20) in a thermal environment, wherein the movable object control unit (33) controls the operation of the movable object (20) to move the movable object to a thermal area (11a, 11b, 11c, or 11d) where the person (13) feels comfortable when the comfort determination unit (32) determines discomfort.

In the first aspect, when the person (13) riding on the movable object (20) feels uncomfortable, the movable object (20) is moved to the thermal area (11a, 11b, 11c, or 11d) where the person (13) feels comfortable. In this way, a thermal environment in which the person (13) in the room (11) feels comfortable can be provided individually.

Specifically, when the person riding on the movable object (20) feels that the room temperature is too high and uncomfortable, the movable object (20) is automatically moved toward the thermal area (11a) having a lower room temperature than the current thermal area (11d). That is, the movable object (20) is merely moved toward the thermal area (11a) having a lower room temperature in advance. Therefore, a thermal environment in which the person (13) feels comfortable can be provided individually in a shorter time than in the case of performing air conditioning control for the temperature around the person (13).

In addition, even when the plurality of movable objects (20) each with the person (13) riding thereon are in the room (11), each of the plurality of movable objects (20) moves toward the optimum thermal area (11a, 11b, 11c, or 11d). Consequently, optimum thermal environments can be provided to the plurality of persons (13).

According to a second aspect, the movable object control system in the first aspect further includes a thermal environment acquisition unit (18) that acquires information indicating a thermal environment in the room (11), wherein the movable object control unit determines the thermal area (11a, 11b, 11c, or 11d) on the basis of the information acquired by the thermal environment acquisition unit.

In the second aspect, the thermal area (11a, 11b, 11c, or 11d) is determined on the basis of the information indicating the thermal environment in the room (11). In this way, for example, which position in the room (11) is in which thermal environment can be grasped and the movable object (20) can be appropriately moved toward the thermal area (11a, 11b, 11c, or 11d) where the person (13) feels comfortable.

According to a third aspect, in the first or second aspect, a plurality of the movable objects (20) are in the room (11), and the movable object control unit (33) controls positions of the movable objects (20) such that an interval between the movable objects (20) is maintained at a predetermined distance or more.

In the third aspect, the positions of the movable objects (20) are controlled such that the interval between the movable objects (20) is maintained at the predetermined distance or more. In this way, even when the plurality of movable objects (20) are in one thermal area (11a), a comfortable work environment can be provided without causing the persons to feel oppressed because the movable objects (20) are too close to each other.

According to a fourth aspect, the movable object control system in any one of the first to third aspects further includes an air conditioner (15) that performs air conditioning in the room (11), and an air conditioning control unit (31) that controls an operation of the air conditioner (15) such that a plurality of thermal areas (11a, 11b, 11c, and 11d) of different thermal environments are formed in the room (11).

In the fourth aspect, the plurality of thermal areas (11a, 11b, 11c, and 11d) of different thermal environments are formed in the room (11) as a result of the air conditioner (15) performing air conditioning in the room (11). In this way, more thermal areas (11a, 11b, 11c, and 11d) can be formed in the room (11) in accordance with preferences of the plurality of persons (13) and a range from which the plurality of persons (13) each select a thermal environment in which they feel comfortable can be made broader.

According to a fifth aspect, in the fourth aspect, the air conditioning control unit (31) controls the operation of the air conditioner (15) to adjust an area of the thermal area (11a) such that an exclusive area obtained by dividing the area of the thermal area (11a) by the number of movable objects (20) standing by in the thermal area (11a) is greater than or equal to a predetermined value.

In the fifth aspect, the area of the thermal area (11a) is adjusted by using the air conditioner (15) in accordance with the exclusive area for the movable object (20). For example, when four thermal areas (11a, 11b, 11c, and 11d) in which the room temperatures are 22° C., 24° C., 26° C., and 28° C. are formed in the room (11) and a percentage of the persons (13) who feel that the room temperature is too high and uncomfortable is large, the air conditioner (15) is controlled to increase the area of the thermal area (11a) of 22° C. in which the lowest room temperature is set. In this way, a comfortable thermal environment can be provided to a larger number of persons (13).

According to a six aspect, the movable object control system in any one of the first to fifth aspects further includes a biological information acquisition unit (25) that acquires biological information of the person (13) riding on the movable object (20), wherein the comfort determination unit (32) determines comfort on the basis of the biological information acquired by the biological information acquisition unit (25).

In the sixth aspect, the comfort is determined on the basis of the biological information of the person (13). Therefore, the movable object (20) can be automatically moved toward the thermal area (11a) where the person feels comfortable without requiring the person (13) riding on the movable object (20) to determine whether or not he or she is feeling comfortable.

According to a seventh aspect, in the sixth aspect, the biological information includes a heart rate or a respiration rate of the person (13).

In the seventh aspect, it can be determined more accurately whether or not the person (13) is feeling comfortable by using the heart rate or the respiration rate of the person (13) as the biological information.

Specifically, when the temperature in the room (11) is high and the person (13) feels hot, an amount of sweat increases to adjust the body temperature, and the interval between heartbeats decreases and the heart rate or respiration rate increases for the attempt to increase the blood flow rate to the peripheral skin in order to promote radiation of heat from the body.

Conversely, when the temperature in the room (11) is low and the person (13) feels cold, an amount of sweat decreases, and the interval between heartbeats increases and the heart rate or respiration rate decreases for the attempt to decrease the blood flow rate to the peripheral skin in order to suppress radiation of heat from the body.

Thus, it can be determined that the person (13) is feeling uncomfortable when the biological information acquired by the biological information acquisition unit (25), that is, the heart rate or respiration rate of the person (13), is greater than or smaller than the reference heart rate or respiration rate obtained when the person (13) is feeling comfortable.

Advantageous Effects of Invention

According to the aspects of the present disclosure, thermal environments in which the persons (13) in the room (11) feel comfortable can be provided individually.

DESCRIPTION OF EMBODIMENTS

An embodiment of the present invention will be described below with reference to the drawings. Note that the following description of the preferred embodiments is merely illustrative in essence and does not intend to limit the present invention and the applications or uses thereof.

Figure 1:
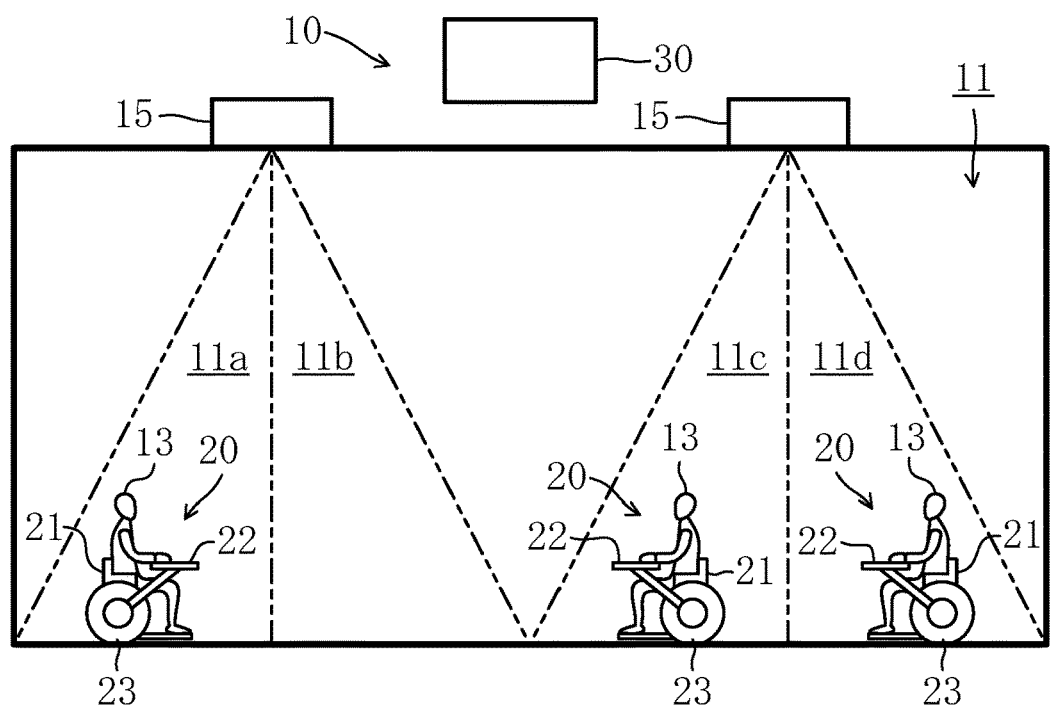
FIG. 1 is a lateral view schematically illustrating a configuration of a control system according to the present embodiment.
Figure 2:
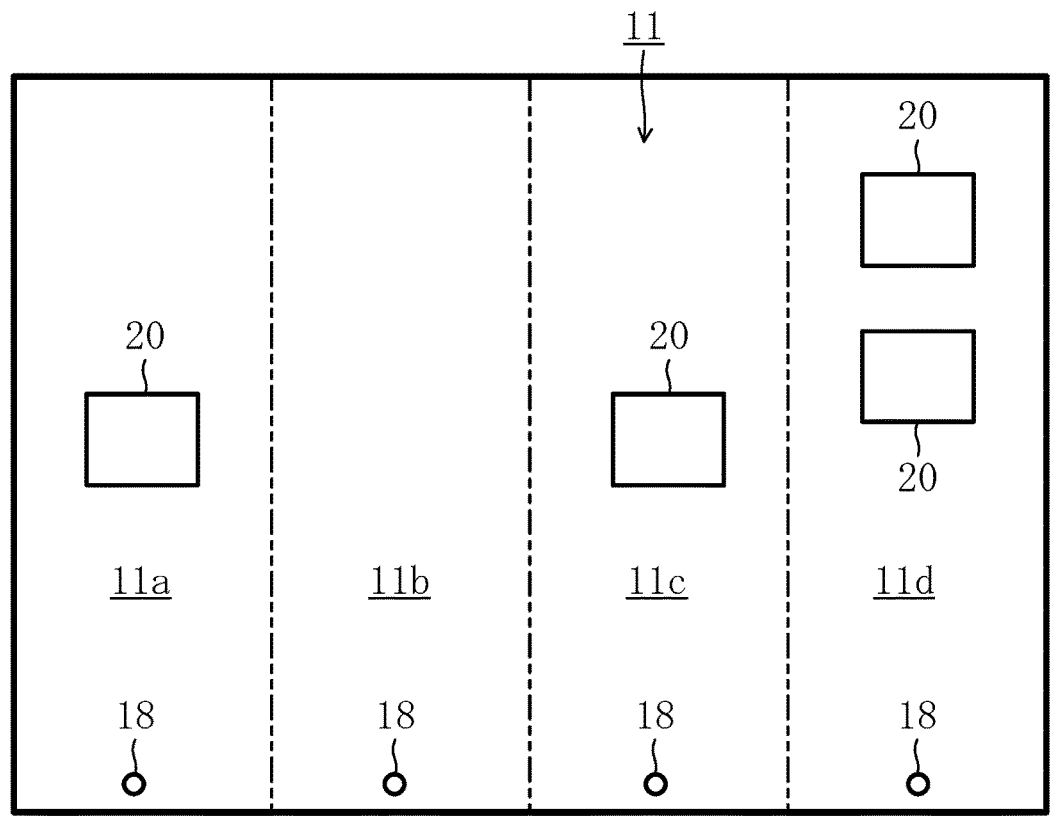
FIG. 2 is a plan view schematically illustrating thermal areas in a room and positions of movable objects.

As illustrated in FIGS. 1 and 2, a control system (10) performs various kinds of control by causing air conditioners (15), movable objects (20), and a controller server (30) to operate in cooperation with one another. The air conditioners (15) each perform air conditioning in a room (11). The movable objects (20) are each movable in the room (11) with a person (13) riding thereon. The controller server (30) controls operations of the air conditioners (15) and the movable objects (20).

The room (11) is assumed to be a free-address office space. The room (11) is not furnished with seats for people, and each person (13) works while riding on the movable object (20) assigned thereto.

The air conditioners (15) are installed near the ceiling of the room (11), and blow out conditioned air to the room (11) so that a plurality of thermal areas (11a, 11b, 11c, and 11d) of different thermal environments are formed in the room (11). In the example illustrated in FIG. 1, four thermal areas (11a, 11b, 11c, and 11d) are formed in the room (11) by using the two air conditioners (15). It is assumed that room temperatures in the thermal areas (11a, 11b, 11c, and 11d) are set to, for example, 22° C., 24° C., 26° C., and 28° C. sequentially from the left side in FIG. 1.

In the room (11), four thermal environment acquisition units (18), each of which is for the corresponding one of the four thermal areas (11a, 11b, 11c, and 11d), are installed. Thus, which position in the room (11) is in which thermal environment can be grasped. The thermal environment acquisition units (18) are assumed to be temperature sensors that detect the room temperature in the present embodiment. However, the thermal environment acquisition units (18)

may be temperature humidity sensors that detect the temperature and humidity in the room (11).

The movable objects (20) each include a seat (21) on which the person (13) sits, a work desk (22) that is provided for the seat (21) and at which the person (13) works, and wheels (23) for moving the seat (21) and the work desk (22). In the example illustrated in FIG. 2, among the movable objects (20), one is in the thermal area (11a) of 22° C., one is in the thermal area (11c) of 26° C., and two are in the thermal area (11d) of 28° C.

Figure 3:
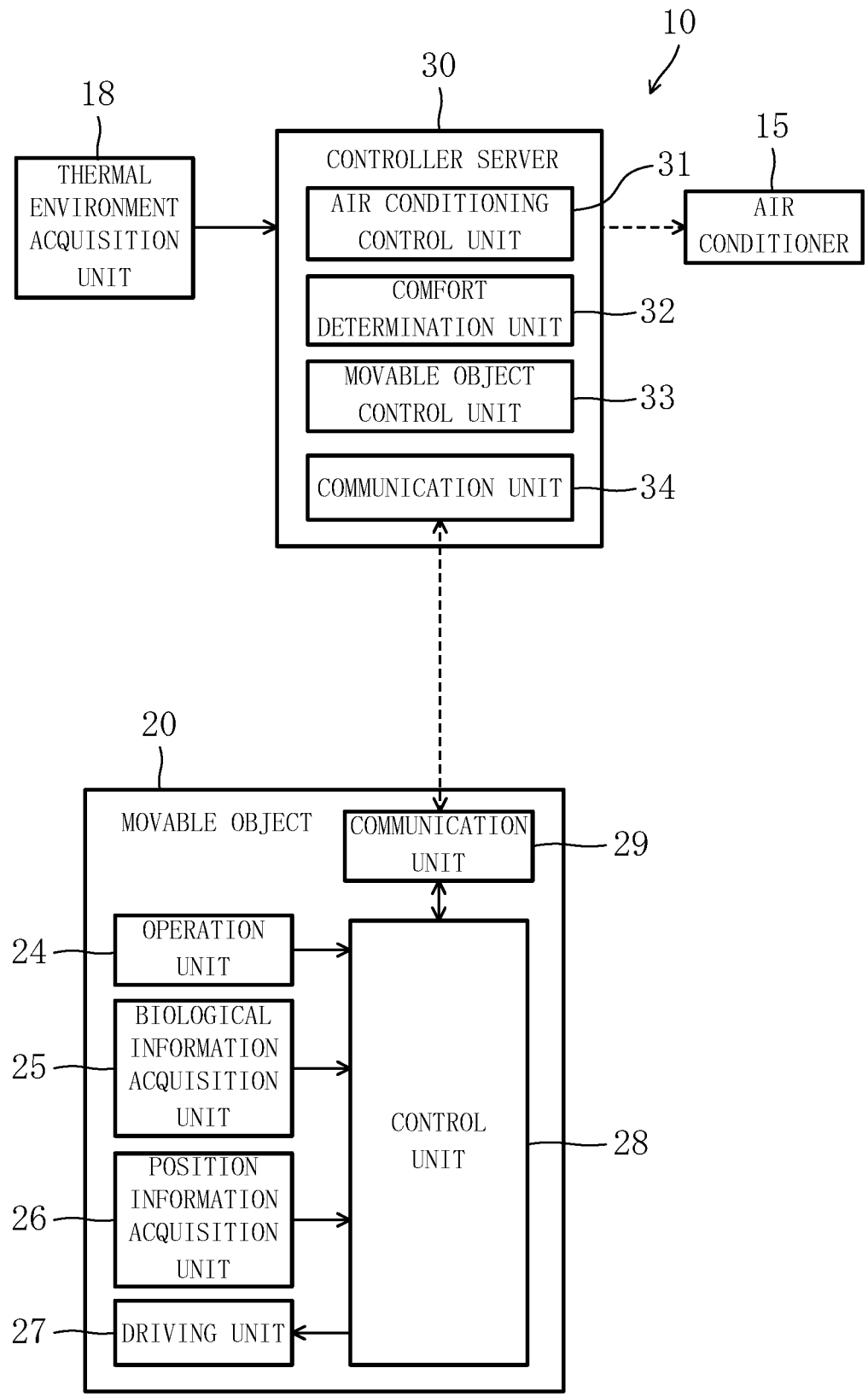
FIG. 3 is a block diagram illustrating the configuration of the control system.

As illustrated in FIG. 3, the movable objects (20) each include an operation unit (24), a biological information acquisition unit (25), a position information acquisition unit (26), a driving unit (27), a control unit (28), and a communication unit (29). The operation unit (24) is used by the person (13) to operate the movable object (20). The biological information acquisition unit (25) acquires biological information of the person (13). The position information acquisition unit (26) acquires position information of the movable object (20) in the room (11). The driving unit (27) drives the wheels (23) to move the movable object (20). The control unit (28) variously controls the movable object (20). The communication unit (29) wirelessly communicates with the controller server (30).

The operation unit (24) includes, for example, a touch-panel monitor, a switch that is a button to be pressed, an operation lever, or the like. The person (13) can move the movable object (20) forward or backward and change the direction by operating the operation unit (24).

The person (13) can also input, by using the operation unit (24), various kinds of information to be sent to the controller server (30). For example, reference vital data (such as the heart rate, the respiration rate, or the body temperature) of the person (13) riding on the movable object (20) in the normal state and preference information indicating whether the person (13) prefers a warm environment or a cool environment are input.

The biological information acquisition unit (25) acquires biological information of the person (13) riding on the movable object (20). The biological information may be, for example, vital data such as the heart rate, the respiration rate, or the body temperature. The biological information acquisition unit (25) includes a watch-type pulsation sensor or body temperature sensor, a pressure-sensitive sensor disposed at the seat (21), or the like. The biological information acquired by the biological information acquisition unit (25) is sent to the control unit (28).

The position information acquisition unit (26) includes, for example, a mobile station (tag) that exchanges a radio wave with a fixed station (sensor) provided in the room (11). The position information acquisition unit (26) acquires the position information of the movable object (20) in the room (11) on the basis of a relative position to the fixed station. The position information acquired by the position information acquisition unit (26) is sent to the control unit (28).

The driving unit (27) includes, for example, a driving motor that rotationally drives the wheels (23). The driving unit (27) drives the wheels (23) on the basis of a control signal from the control unit (28).

The control unit (28) receives various kinds of data from the operation unit (24), the biological information acquisition unit (25), and the position information acquisition unit (26), and sends the various kinds of data to the controller server (30) via the communication unit (29). The control unit (28) also controls the operation of the driving unit (27) on the basis of a control signal from the controller server (30).

The controller server (30) includes an air conditioning control unit (31), a comfort determination unit (32), a movable object control unit (33), and a communication unit (34). The air conditioning control unit (31) controls the operation of the air conditioner (15). The comfort determination unit (32) determines whether or not the person (13) riding on the movable object (20) is feeling comfortable. The movable object control unit (33) controls the operation of the movable object (20). The communication unit (34) wirelessly communicates with the movable object (20).

The controller server (30) receives signals indicating temperatures in the respective thermal areas (11a, 11b, 11c, and 11d) acquired by the thermal environment acquisition units (18). Thus, the controller server (30) can determine the thermal environments in the room (11).

The air conditioning control unit (31) outputs a control signal to the air conditioner (15) to control the operation of the air conditioner (15) so that the thermal areas (11a, 11b, 11c, and 11d) in the room (11) have the respective set temperatures.

The comfort determination unit (32) determines the comfort of the person (13) riding on the movable object (20) in the thermal environment, on the basis of the biological information sent from the movable object (20).

Specifically, when the temperature in the room (11) is high and the person (13) feels hot, an amount of sweat increases to adjust the body temperature, and the interval between heartbeats decreases and the heart rate or respiration rate increases for the attempt to increase the blood flow rate to the peripheral skin in order to promote radiation of heat from the body.

Conversely, when the temperature in the room (11) is low and the person (13) feels cold, an amount of sweat decreases, and the interval between heartbeats increases and the heart rate or respiration rate decreases for the attempt to decrease the blood flow rate to the peripheral skin in order to suppress radiation of heat from the body.

Thus, the comfort determination unit (32) can determine that the person (13) is feeling uncomfortable by determining whether the heart rate or respiration rate of the person (13) is greater than or smaller than the reference heart rate or respiration rate obtained when the person (13) is feeling comfortable.

The movable object control unit (33) remotely operates the movable object (20) to move the movable object (20) to the thermal area (11a, 11b, 11c, or 11d) where the person (13) feels comfortable when the discomfort is determined by the comfort determination unit (32).

Figure 4:
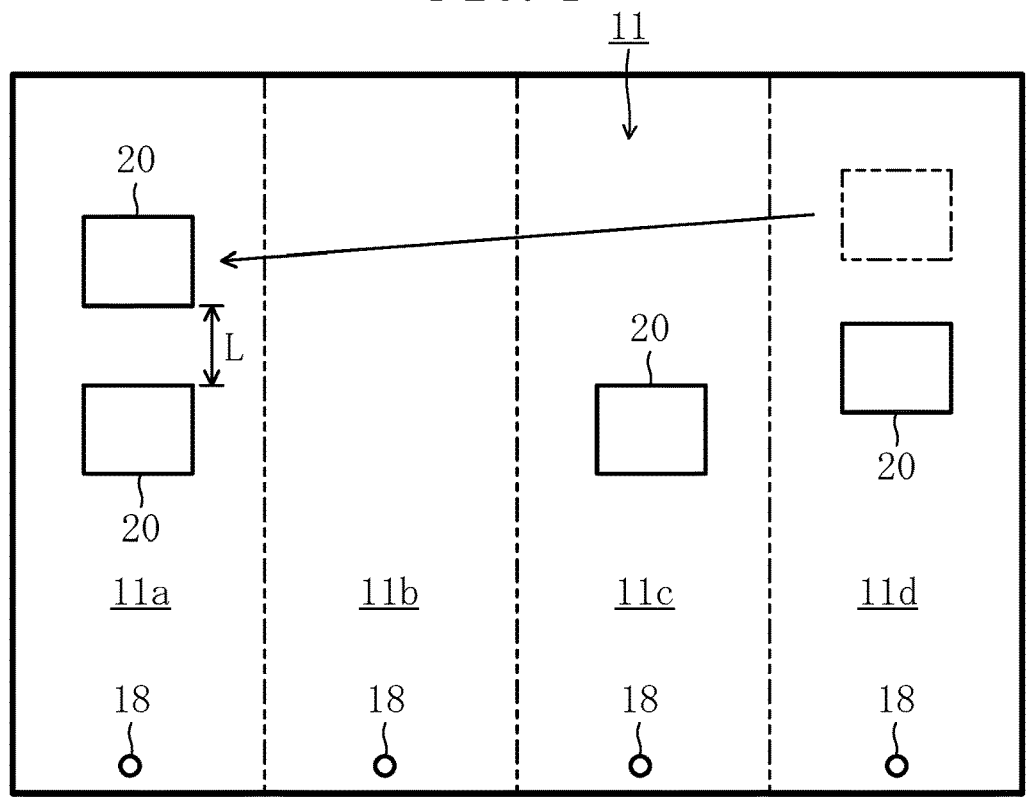
FIG. 4 is a plan view schematically illustrating the thermal areas in the room and the positions of the movable objects in the case where the movable object is moved.

For example, as illustrated in FIG. 4, suppose that the person (13) riding on the movable object (20) standing by in the thermal area (11d) in which the room temperature is set to 28° C. feels that the room temperature is too high and uncomfortable. In such a case, the movable object (20) is automatically moved toward the thermal area (11a) having a lower room temperature of 22° C. than the current thermal area (11d).

As described above, the movable object (20) is merely moved toward the thermal area (11a) of 22° C. having a lower room temperature in advance. Therefore, a thermal environment in which the person (13) feels comfortable can be provided individually in a shorter time than in the case of performing air conditioning control for the temperature around the person (13).

When a plurality of movable objects (20) are present in the thermal area (11a) and the movable objects (20) are too close to each other, the persons (13) may feel oppressed, which is not preferable.

Accordingly, as illustrated in FIG. 4, when another movable object (20) is standing by in the thermal area (11a) that is the destination, the positions of the movable objects (20) are controlled such that an interval (L) between the movable objects (20) is maintained at a predetermined distance or more. In this way, a work environment in which each person feels comfortable can be provided even when a plurality of movable objects (20) are present.

In addition, suppose that the person (13) in the thermal area (11d) of 28° C. and the person (13) in the thermal area (11c) of 26° C. illustrated in FIG. 4 also feel that the room temperature is too high and uncomfortable and desire to move to the thermal area (11a) of 22° C. In such a case, four movable objects (20) crowd in the thermal area (11a) of 22° C.

Figure 5:
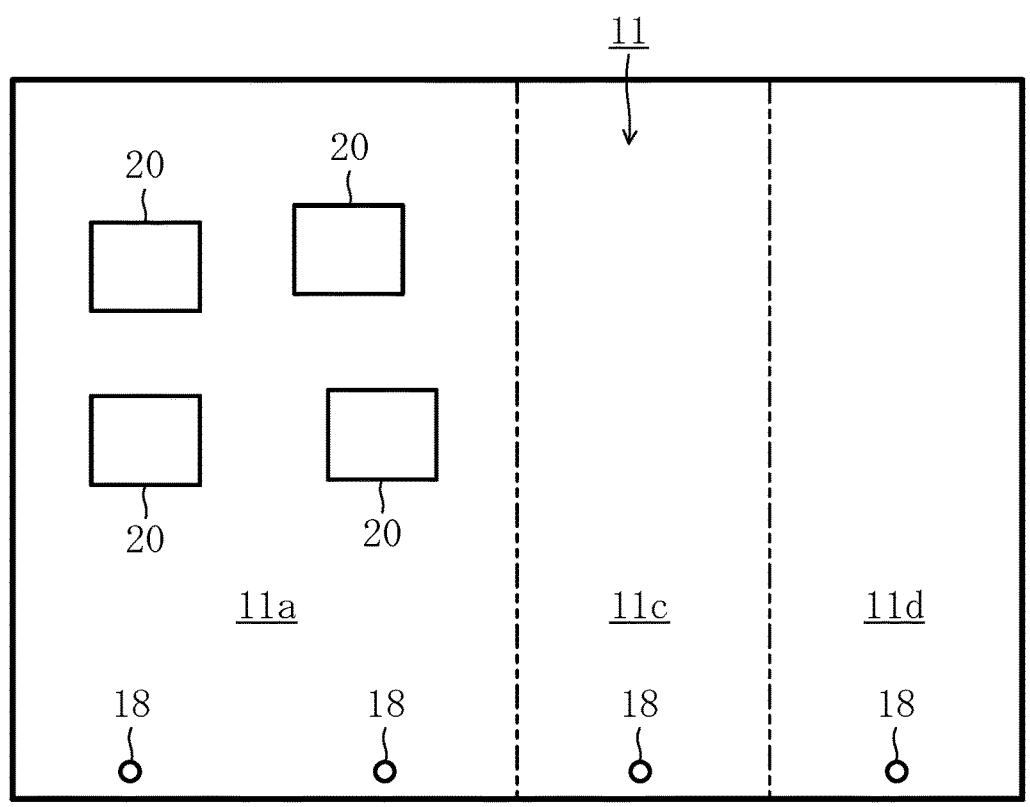
FIG. 5 is a plan view in the case where the thermal area is extended.

In this case, the air conditioning control unit (31) controls the operations of the air conditioners (15) to adjust the area of the thermal area (11a) so that an exclusive area obtained by dividing the area of the thermal area (11a) of 22° C. by the number of movable objects (20) standing by in this thermal area (11a) is greater than or equal to a predetermined value, for example, the thermal area (11a) of 22° C. extends over the thermal area (11b) of 24° C. as illustrated in FIG. 5. In this way, a comfortable thermal environment can be provided to a larger number of persons (13).

Other Embodiments

The embodiment described above may be configured as follows.

In the present embodiment, the comfort is determined on the basis of the biological information of the person (13) to enable the movable object (20) to be automatically moved toward the thermal area (11a, 11b, 11c, or 11d) where the person (13) feels comfortable without requiring the person (13) riding on the movable object (20) to determine whether or not he or she is feeling comfortable; however, the configuration is not limited to this form.

For example, the person (13) may declare whether or not he or she is comfortable by operating the operation unit (24) of the movable object (20). Then, the movable object control unit (33) may remotely operate the movable object (20) on the basis of this self-declaration result.

In addition, in the present embodiment, for example, when it is determined that the thermal area (11d) of 28° C. is too hot, the movable object (20) is moved toward the thermal area (11a) of 22° C.; however, the configuration is not limited to this form.

The movable object (20) may be moved to the thermal area of a lower room temperature step by step. For example, the comfort determination unit (32) may again determine the comfort after the movable object (20) is moved from the thermal area (11d) of 28° C. to the thermal area (11c) of 26° C. If the comfort is determined, the movable object (20) stands by in the thermal area (11c) of 26° C. If the discomfort is determined, the movable object (20) is moved to the thermal area (11b) of 24° C. or the like.

In addition, in the present embodiment, the plurality of thermal areas (11a, 11b, 11c, and 11d) of different room temperatures are mainly formed in the room (11); however, the configuration is not limited to this form.

For example, thermal areas of different room temperatures and different humidity values or thermal areas of different thermal environment evaluation indices (PMV: Predicted Mean Vote) that associate a heat load of the body with the warm-cold sense of the person may be formed, and the movable object (20) may be moved to the thermal area where the person (13) feels comfortable.

In addition, in the present embodiment, the heart rate or the respiration rate of the person (13) is used as the biological information. In addition to these, for example, an image of the facial expression of the person (13) may be captured with a camera, image processing may be performed on the resultant image to determine the stress, and it may be determined whether or not the person (13) is feeling comfortable from the stress determination result.

In addition, in the present embodiment, the plurality of thermal areas (11a, 11b, 11c, and 11d) of different thermal environments are formed in the room (11) by controlling the operations of the air conditioners (15). However, for example, if the plurality of thermal areas are naturally formed in the room (11) without operating the air conditioners (15) as a result of air becoming warm near the window due to the sunlight incident to the room (11) or the like, the movable object (20) may be moved to these thermal areas.

INDUSTRIAL APPLICABILITY

As described above, the present invention is highly useful and the industrial applicability thereof is high because highly practical effects that thermal environments in which persons in a room feel comfortable can be provided individually are obtained.

REFERENCE SIGNS LIST 10 control system
11 room
11a-11b thermal area
13 person
15 air conditioner
18 thermal environment acquisition unit
20 movable object
25 biological information acquisition unit
31 air conditioning control unit
32 comfort determination unit
33 movable object control unit

The invention claimed is:

1. A movable object control system including a movable object movable in a room with a person riding thereon, the movable object control system comprising:
 a controller programmed to control operation of the movable object by
  obtaining biometric information of the person riding on the movable object from at least one biometric sensor while the movable object is in one thermal area within the room,
  using the obtained biometric information to estimate a level of comfort of the person riding on the movable object as either being comfortable or uncomfortable, and
  in response to estimating the level of comfort as being uncomfortable, determining a modification to thermal conditions of the one thermal area based on the obtained biometric information, and controlling the operation of the movable object to move the movable object to another one of the thermal areas in the room exhibiting a difference in thermal conditions relative to the first thermal area where said difference corresponds to the determined modification.

2. The movable object control system according to claim 1, further comprising:

thermal sensors that acquire information indicating different thermal environments in the room, wherein
the controller determines the another one of the thermal areas on the basis of the information acquired by the at least one sensor.

3. The movable object control system according to claim 1, wherein
a plurality of the movable objects are in the room, and
the controller controls positions of the movable objects such that an interval between the movable objects is maintained at a predetermined distance or more.

4. The movable object control system according to claim 1, further comprising:
an air conditioner that performs air conditioning in the room; and
an air conditioning controller that controls an operation of the air conditioner such that a plurality of thermal areas are formed in the room.

5. The movable object control system according to claim 4, wherein
multiple movable objects are present in the room, and the air conditioning control unit controls the operation of the air conditioner to extend one area of the thermal areas in case an exclusive area obtained by dividing the area of the thermal area by the number of movable objects standing by in the one area of the thermal areas is greater than or equal to a predetermined value.

6. The movable object control system according to claim 1, wherein
the obtained biometric information includes a heart rate or a respiration rate of the person riding on the corresponding movable object.

* * * * *